United States Patent [19]
Kilbey

[11] Patent Number: 5,814,000
[45] Date of Patent: Sep. 29, 1998

[54] ADJUSTABLE JOINT BRACE

[75] Inventor: Bryan Kilbey, DeFuniak Springs, Fla.

[73] Assignee: Professional Products, Inc., DeFuniak Springs, Fla.

[21] Appl. No.: 679,188

[22] Filed: Jul. 12, 1996

[51] Int. Cl.⁶ ..................................................... A61F 5/00
[52] U.S. Cl. .............................................. 602/16; 602/26
[58] Field of Search ................... 602/5, 16, 20, 602/23, 26

[56] References Cited

U.S. PATENT DOCUMENTS

| | | | |
|---|---|---|---|
| 4,817,588 | 4/1989 | Bledsoe | 602/16 |
| 5,000,169 | 3/1991 | Swicegood et al. | 602/16 |
| 5,052,379 | 10/1991 | Airy et al. | 602/16 |
| 5,292,303 | 3/1994 | Bastyr et al. | 602/16 |
| 5,399,154 | 3/1995 | Kipnis et al. | 602/16 X |
| 5,409,449 | 4/1995 | Nebolon | 602/26 X |
| 5,437,611 | 8/1995 | Stern | 602/26 X |
| 5,443,444 | 8/1995 | Pruyssers | 602/16 X |
| 5,460,599 | 10/1995 | Davis et al. | 602/26 |

*Primary Examiner*—Linda C. Dvorak
*Attorney, Agent, or Firm*—George A. Bode; Michael L. Hoelter; Bode & Associates

[57] ABSTRACT

A pivotable brace for adjustably supporting a user's joint, such as a knee joint, at a variety of different angles as desired. The restraint imposed by this brace upon the joint can also be released thereby permitting the joint to further bend or flex as needed but which will return to its original setting by returning the joint back to its originally braced position. Preferably, a pair of such braces will be secured to opposite sides of the joint to be braced for maximum support and restraint.

14 Claims, 8 Drawing Sheets

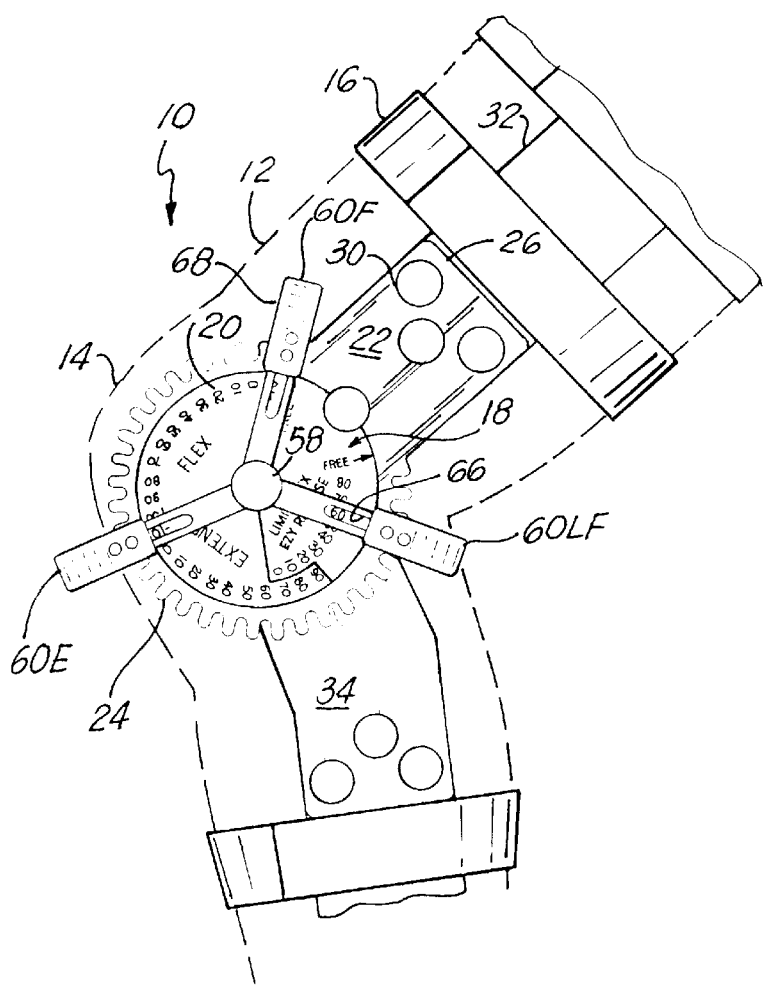
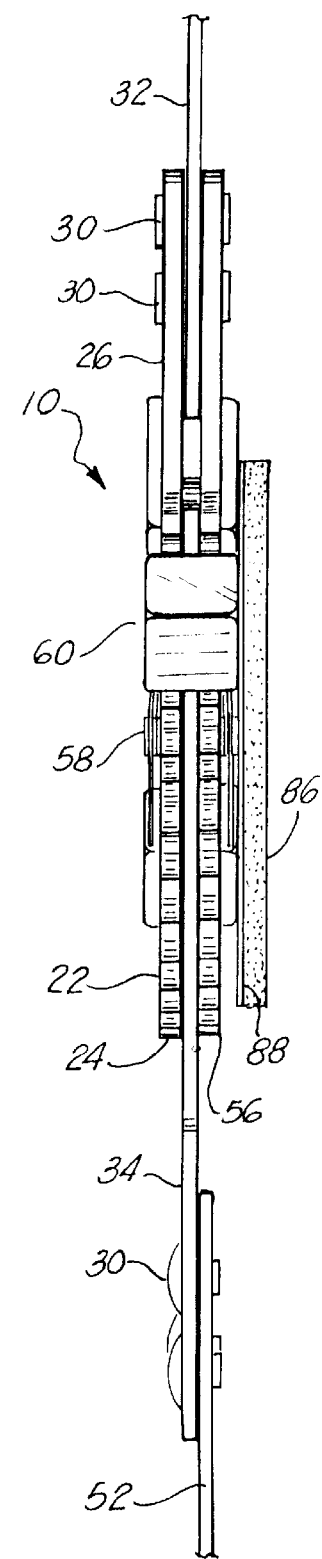
FIG. 1
FIG. 8

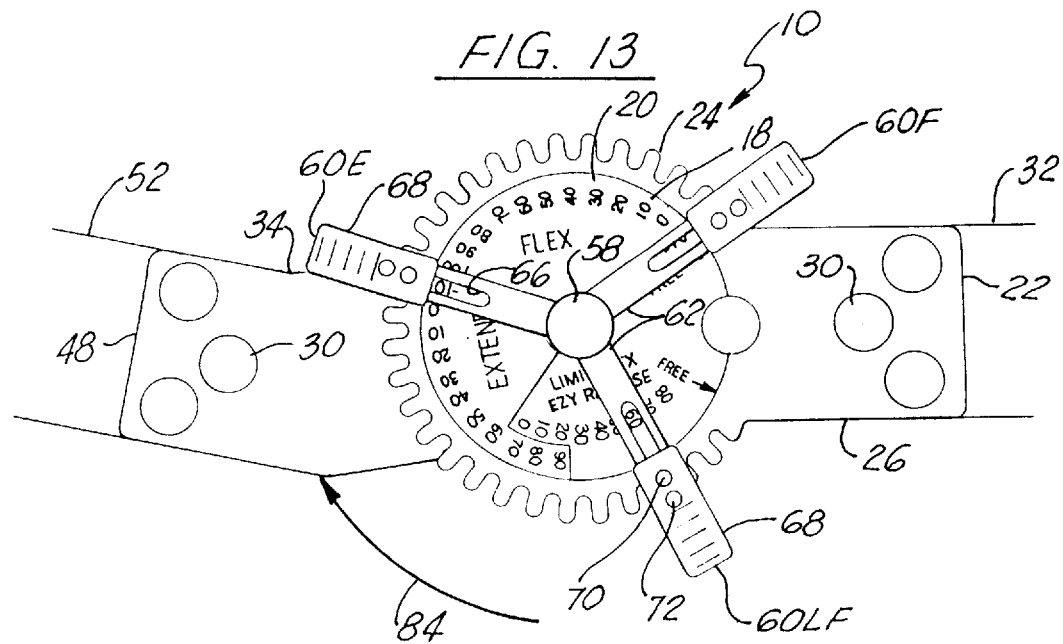
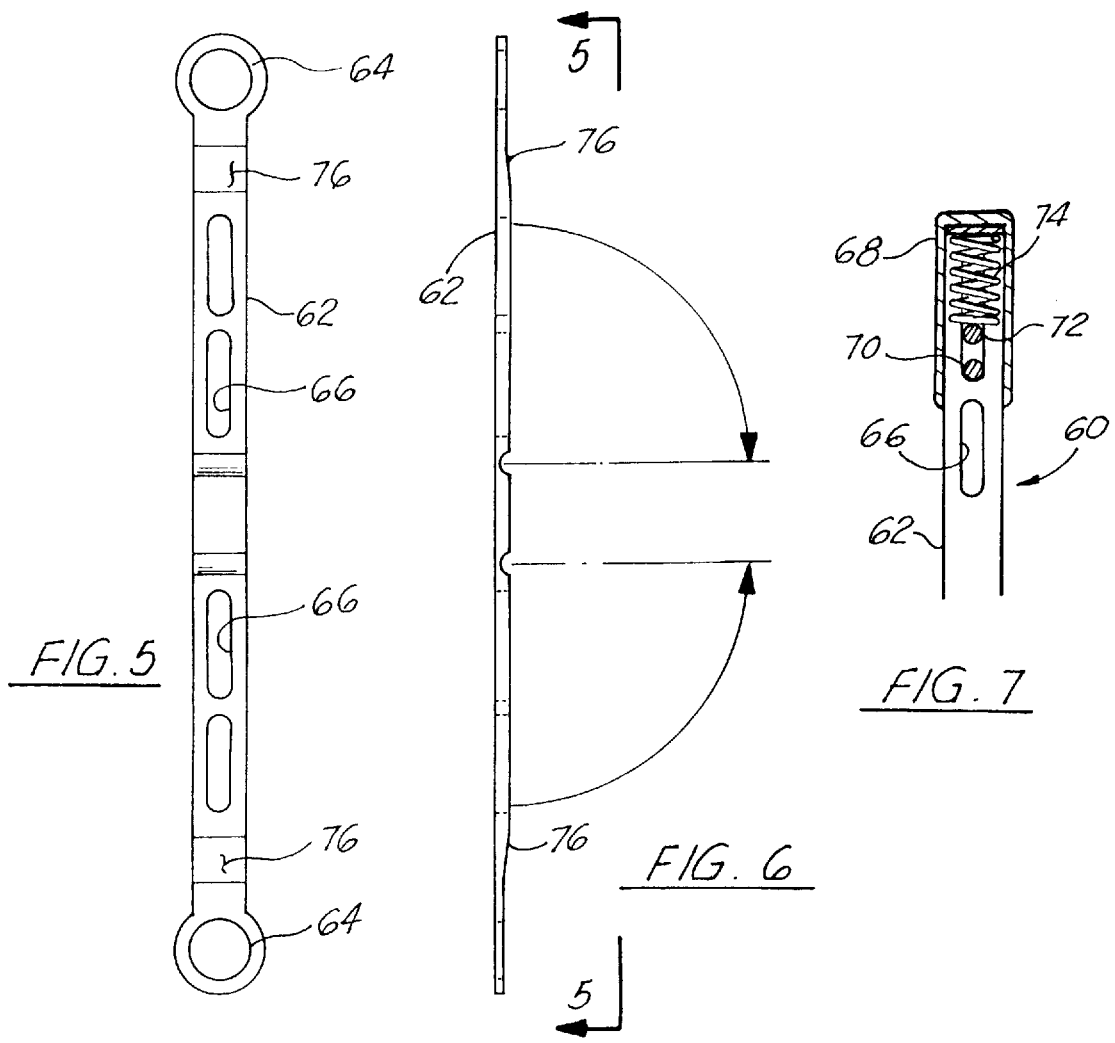

ADJUSTABLE JOINT BRACE

BACKGROUND OF THE INVENTION

1. Field of the Invention

This invention pertains to medical devices in general and, more particularly, to an adjustable brace for use in supporting as well as restricting the rotation of an injured joint, such as a knee joint.

2. General Background

While it is well known that an injured joint requires support during recuperation, some methods restrict the mobility or rotation of the joint more than others. For example, if the injury is such that no bending of the joint is permitted, it was often common to install a cast or splint around the joint so as to physically prevent any such movement or rotation. This rigid cast or splint, however, made it rather difficult for the patient to bend the joint when it became necessary to do so.

On the other extreme, however, support for an injured joint was sometimes provided simply by wrapping the joint in a bandage or the like. This made it easier for the patient to bend the joint, but it did little to immobilize the joint during recuperation.

It is thus an object of this invention to provide a joint brace that not only provides rigid support when needed (i.e. will prevent any unwanted bending thereof), but can also be adjusted so as to permit an occasional bending of the joint when it becomes necessary to do so. It is another object of this invention to provide a means of restricting the bending or rotation of the joint to within a certain desired range of motion should the injury tolerate such. Another object of the invention is to provide a means of supporting and bracing a joint within the range desired by the medical profession while also enabling the patient to suspend or override such restrictions when it becomes imperative for this occur. Yet another object of this invention is to enable the patient to automatically return to the preset degree of support for the joint immediately after such restrictions have temporarily been suspended. These and other objects and advantages of this invention will become obvious upon further investigation.

SUMMARY OF THE PRESENT INVENTION

The preferred embodiment of the apparatus of the present invention solves the aforementioned problems in a straightforward and simple manner. This invention pertains to an adjustable joint brace having a first gear member configured with a plurality of gear teeth along at least a portion of its outer periphery. Pivotally secured around this first gear member are a plurality of sliding latches that rotate with respect to the first gear member and which engage the gear teeth of the gear member. Each sliding latch comprises locking means for removable locking the sliding latch with respect to selected gear teeth. An elongated support is pivotally secured adjacent the first gear member and is configured to engage the locking means of the sliding latch means. These locking means restrict the rotation of the elongated support with respect to the first gear member. This brace is secured around the user's joint via an adjustable securing assembly.

BRIEF DESCRIPTION OF THE DRAWING

For a further understanding of the nature and objects of the present invention, reference should be had to the following description taken in conjunction with the accompanying drawing in which like parts are given like reference numerals and, wherein:

FIG. 1 is a front pictorial view of the invention in a fixed brace position as applied to the knee of a patient;

FIG. 5 is an enlarged pictorial view of one embodiment of the pivotal member which comprises a part of the sliding latch mechanism;

FIG. 6 is an enlarged side view of the embodiment of FIG. 5 illustrating how it is bent;

FIG. 7 is a pictorial view, partially cut away, of the sliding latch mechanism of the invention;

FIG. 8 is a side view of the invention;

FIG. 13 is a front pictorial view of the invention illustrating how the brace automatically returns to its original preset conditions after such restrictions were temporarily suspended; and, FIG. 14 is a pictorial view of the invention similar to that shown in FIG. 13, but with a portion of the invention cut away.

DETAILED DESCRIPTION OF THE PREFERRED EMBODIMENT

Figure 2:
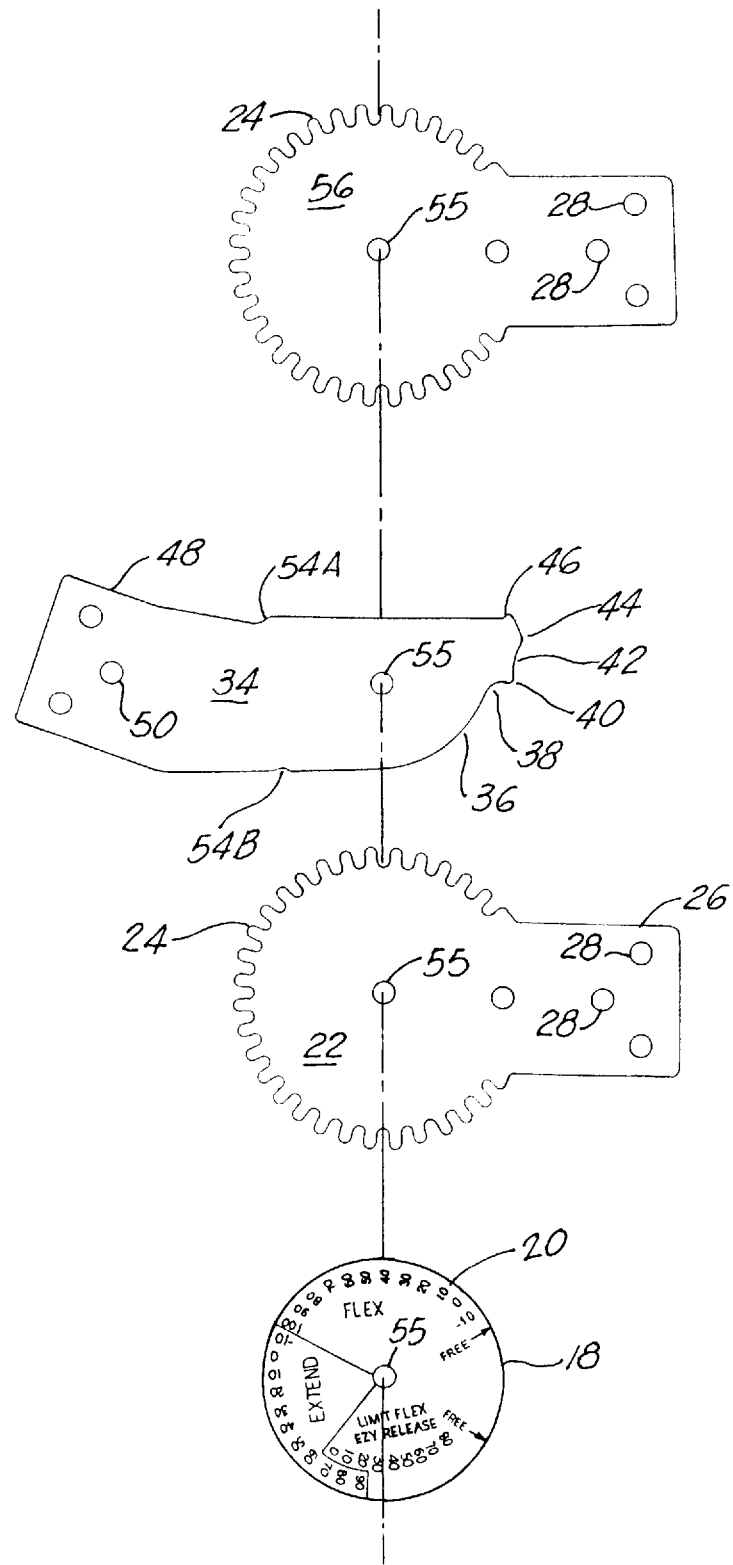
FIG. 2 is an exploded view of the gear components of the invention.
Figure 3:
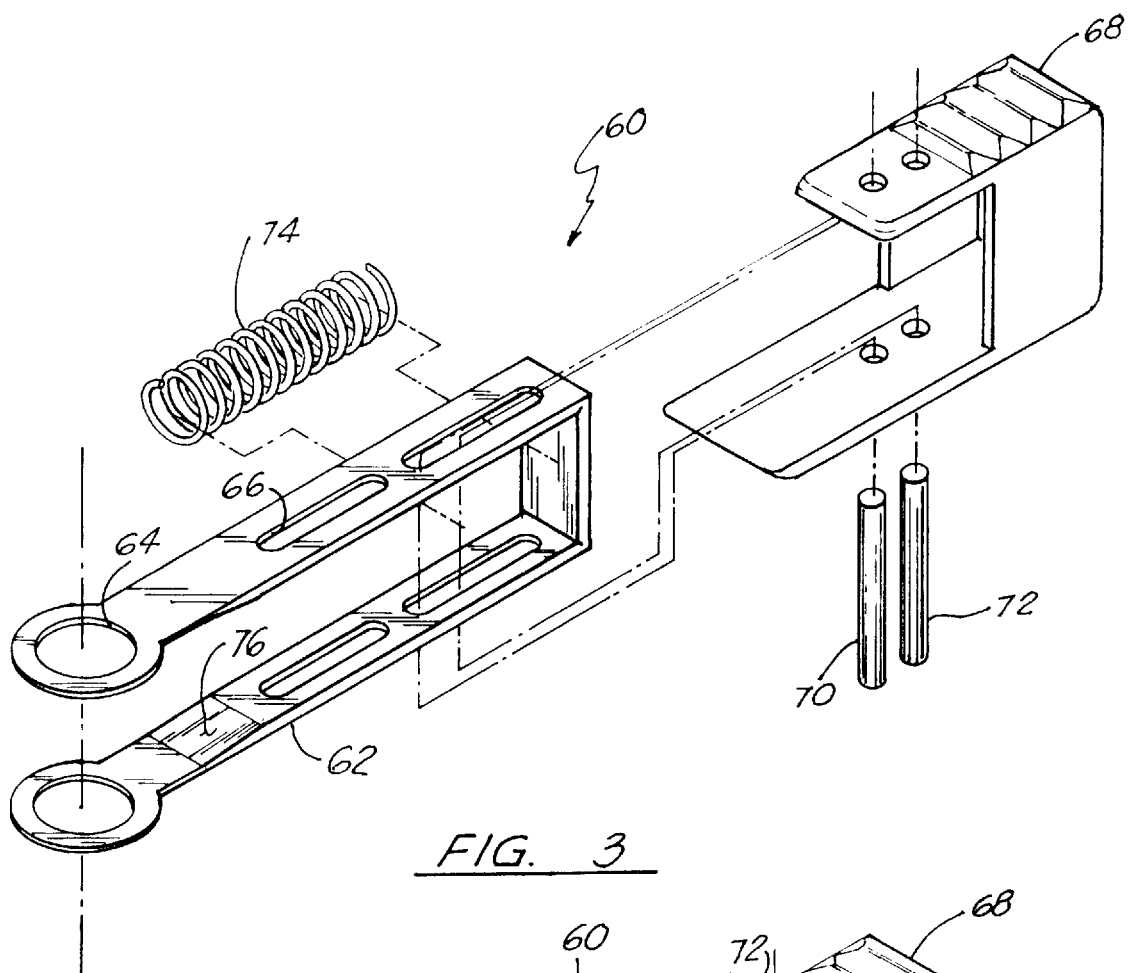
FIG. 3 is an exploded view of the sliding latch mechanism of the invention.

Referring initially to FIG. 1, there is shown brace 10 properly strapped to user's leg 12 both above and below knee 14. Of course, brace 10 may also be secured adjacent other joints of the user, knee 14 being selected herein for descriptive purposes only. In this embodiment, brace 10 is secured in place via a series of hook and loop closure straps 16 which encircle leg 12, but other means of affixing brace 10 to leg 12 can also be implemented. Furthermore, while not illustrated here, it is also generally good practice to secure two separate braces 10 on opposite sides of knee 14 for maximum support and protection. These oppositely located braces 10 would, of course, be mirror images of each other.

Brace 10 is generally constructed of a rigid metal substance such as aluminum, steel, or stainless steel for rigidity and strength. However, brace 10 can be constructed of other material if the strain placed upon brace 10 will not be too great or if this other material has characteristics that match those required for brace 10. However, the material of construction of brace 10 is of limited importance so long as it is of sufficient strength to withstand the repeated stresses imparted to it by the user.

The actual configuration of the various components of brace 10 is better illustrated in FIG. 2. As shown, brace 10 comprises an outer decal 18 having a series of indica 20 marked thereon. The importance of such indica 20 and the actual operation of brace 10 will be described below. This decal 18 will preferably be permanently attached to first or outer gear member 22.

Outer gear 22 is partially encircled by evenly distributed teeth 24 along its outer perimeter. The remainder of gear 22 is configured as an extension 26 having a series of openings 28 therein. As indicated in FIG. 8, rivets or screws or other securing means 30 pass through these openings 28 to secure gear 22 to longer support member 32. This longer support member 32 is generally bent or tapered so as to more closely conform to the user's leg 12 to which it is strapped. Thus, it can be said that gear 22 remains relatively stationary and in alignment with the user's leg 12 above knee 14. Also as indicated in FIG. 8, gear 22 is planar in construction and of generally uniform thickness throughout its length.

Next is lower leg support 34 that would abut gear 22. Support 34 is also planar in construction and of generally uniform thickness so that it can rotate with respect to gear 22 without engaging teeth 24. End 36 of support 34 is specially configured with carefully arranged concave and sloped surfaces therein. First concavity 38 in end 36 terminates in stop 40 that slightly projects from support 34. Sloping away from stop 40 is tapered surface 42 which incorporates bulge 44 intermediate stop 40 and recess 46. The importance and function of this unique configuration of support 34 will be described below.

Opposite end 36 of support 34 is lower leg extension 48. This extension 48 also incorporates a series of openings 50 therein through which a series of rivets or the like 30 pass. These rivets 30 secure extension 48 to longer support member 52 in the typical fashion as illustrated in FIG. 8. This longer support member 52, similar to support member 32, is also generally bent or tapered so as to more closely conform to the shape of user's leg 12. Thus, lower leg support 34 is held or retained in alignment with the user's leg 12 below knee 14 as indicated in FIG. 1.

A pair of notches 54A and 54B are formed on opposite sides of support 34 intermediate end 36 and extension 48. The proper location and function of notches 54A and 54B will be more fully described below. Generally, however, the curvature of notches 54A and 54B will be similar to that of first concavity 38 and recess 46 since they will all be engaging similarly sized pins. Also, notches 54A and 54B, first concavity 38, and recess 46 are all radially spaced generally equal distances from center opening 55.

Second or inner gear member 56 is constructed identical to first or outer gear member 22 and the two are secured in alignment together via rivets 30 as shown in FIG. 8. These rivets also sandwich longer support member 32 between gear members 22 and 56. Additionally, lower leg support 34 is pivotally supported between gear members 22 and 56 via center rivet 58 passing through center opening 55 as indicated in FIG. 2. In this fashion, while gear members 22 and 56 remain fixed with respect to each other, lower leg support 34 is pivotable and can rotate with respect to such gear members via center rivet 58.

Referring now to FIGS. 3–7, there is shown the construction of sliding latch 60 which controls the permitted range of motion (if any) between lower leg support 34 and gear members 22 and 56. In FIG. 1, three such sliding latches 60 are illustrated, but there may actually be more or fewer such latches as needed. These three sliding latches 60 are individually identified as extension sliding latch 60E, flex sliding latch 60F, and limit flex sliding latch 60LF. These sliding latches 60 respectively control the extension, flex, and maximum permitted flex of knee 14. Normally extension sliding latch 60E would be colored differently from flex sliding latch 60F so as to aid in distinguishing between them since they are both generally on the same side of brace 10.

Figure 4:
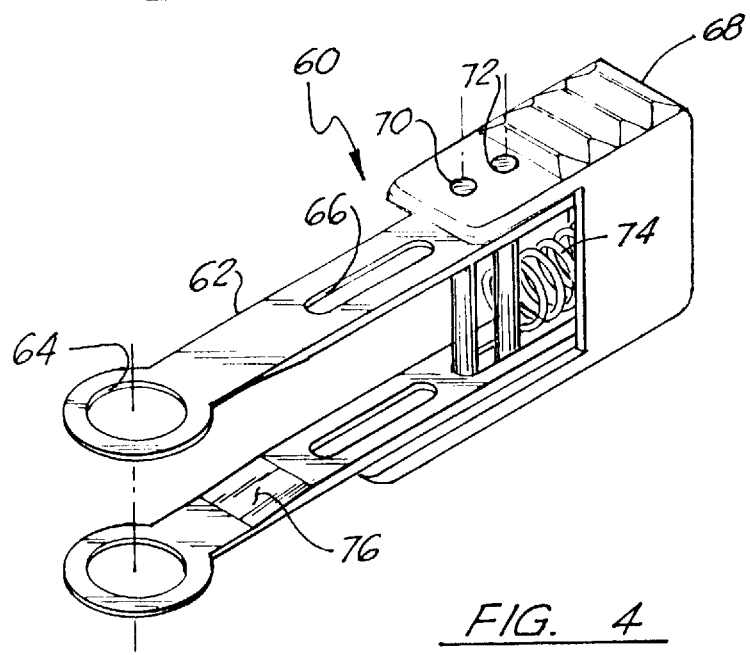
FIG. 4 is an enlarged assembled view of the sliding latch mechanism of the invention.

As indicated, each sliding latch 60 comprises a bent lockout strap 62 having opposite end openings 64 that are sized to accept center rivet 58 therethrough. Also, each such lockout strap 62 is further configured with a series of elongated slots 66 therein which assist in the movement of latch 60 about center rivet 58. A cap 68 fits over the bent portion of lockout strap 62 as indicated and its outer surface may be roughened or contoured so as to ease the grasping of this cap 68 by the user. Inner and outer pins 70 and 72 are secured in openings in this cap 68 and these pins 70 and 72 also pass through oppositely spaced elongated openings 66 within lockout strap 62 as indicated. A spring 74 is compressed to fit between the inside of cap 68 and outer pin 72 as indicated in FIG. 7. Each sliding latch 60 is assembled as shown in FIG. 4 and is then pivotally secured around brace 10 via center rivet 58 as indicated in FIG. 1. Of course, in order to accommodate three such sliding latches 60, the ends of each lockout strap 62 may be tapered 76 to as to reduce its thickness adjacent center rivet 58.

Figure 9:
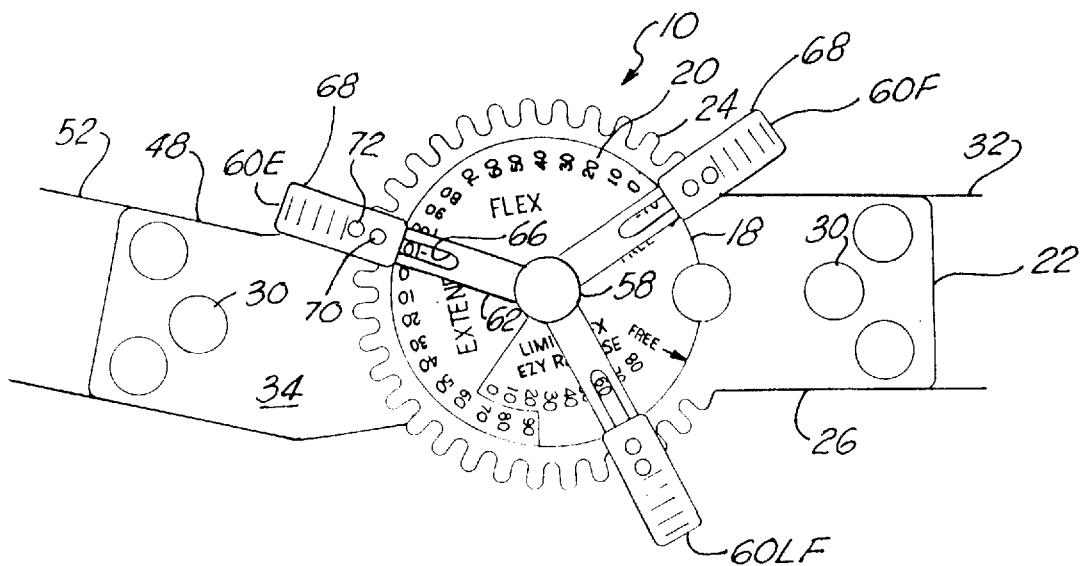
FIG. 9 is a front pictorial view of the invention illustrating the brace in a locked position at negative ten degrees.
Figure 10:
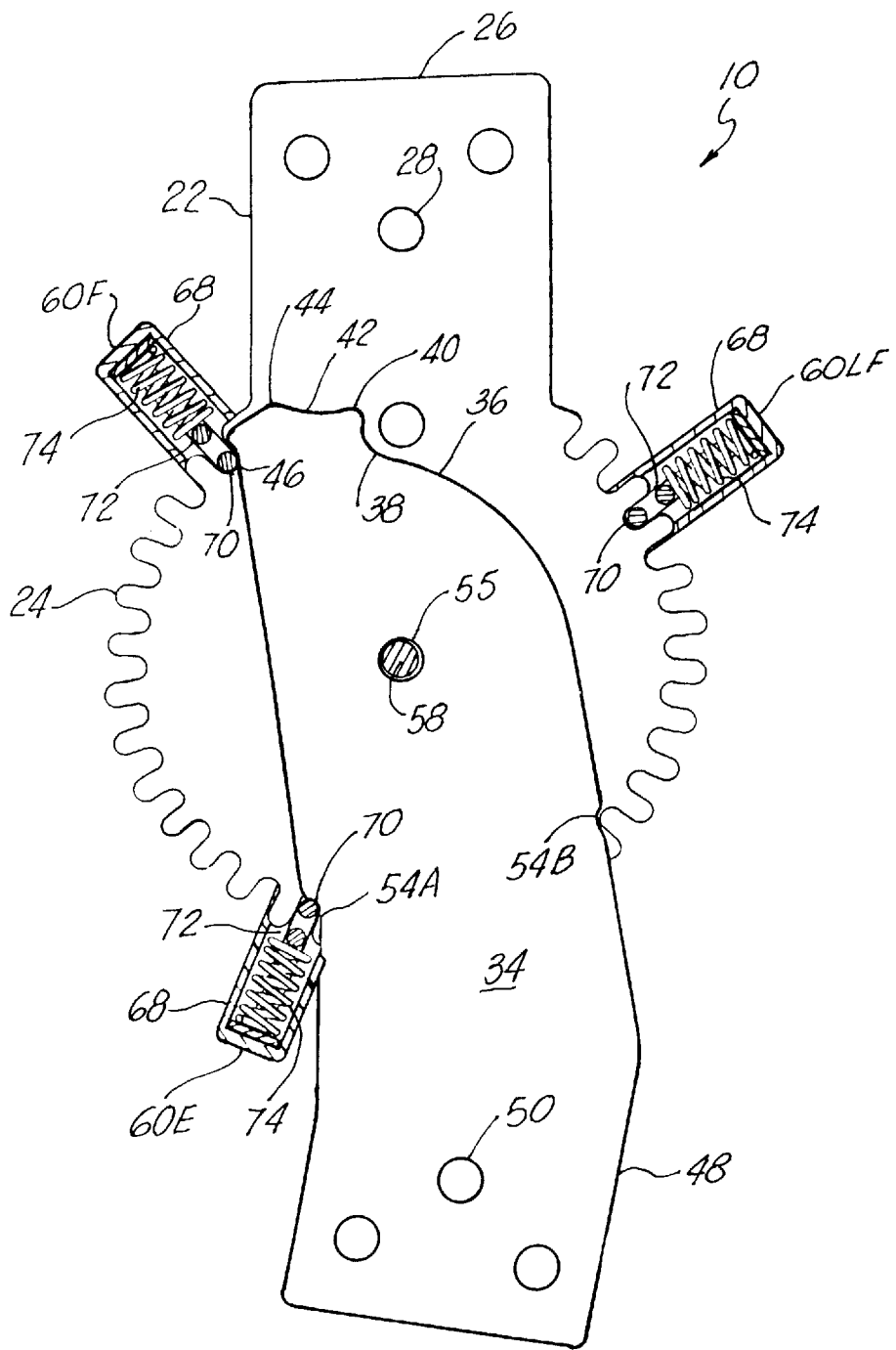
FIG. 10 is a pictorial view of the invention similar to that shown in FIG. 9, but with a portion of the invention cut away.

Referring now to FIGS. 9 and 10, extension and flex sliding latches 60E and 60F are positioned so as to retain brace 10 in a locked position. This effectively prevents knee 14 from bending and retains leg 12 at the angle set by these extension and flex sliding latches 60E and 60F. In FIGS. 9 and 10, the angle set is negative 10 degrees (−10) since both extension and flex sliding latches 60E and 60F are both set at this position. Such position can be confirmed by viewing indica 20 through elongated slot 66 in each such latch 60. As can be seen in FIG. 10, brace 10 is retained in this position by the insertion of inner pin 70 of both extension and flex sliding latches 60E and 60F between the appropriate teeth 24 of inner and outer gear members 22 and 56.

This locked position of brace 10 is maintained by inner pin 70 of extension sliding latch 60E engaging notch 54A of lower leg support 34 thereby preventing this support 34 from any further rotation in the clockwise direction. Likewise, inner pin 70 of flex sliding latch 60F engages recess 46 of lower leg support 34 thereby preventing this support 34 from any further rotation in the counter-clockwise direction. Hence, lower leg support 34 is effectively restrained in a fixed position with respect to gear members 22 and 56. Consequently, brace 10 effectively retains knee 14 at this preset angle and permits no rotation or movement of knee 14 when brace 10 is in this locked position.

Figure 11:
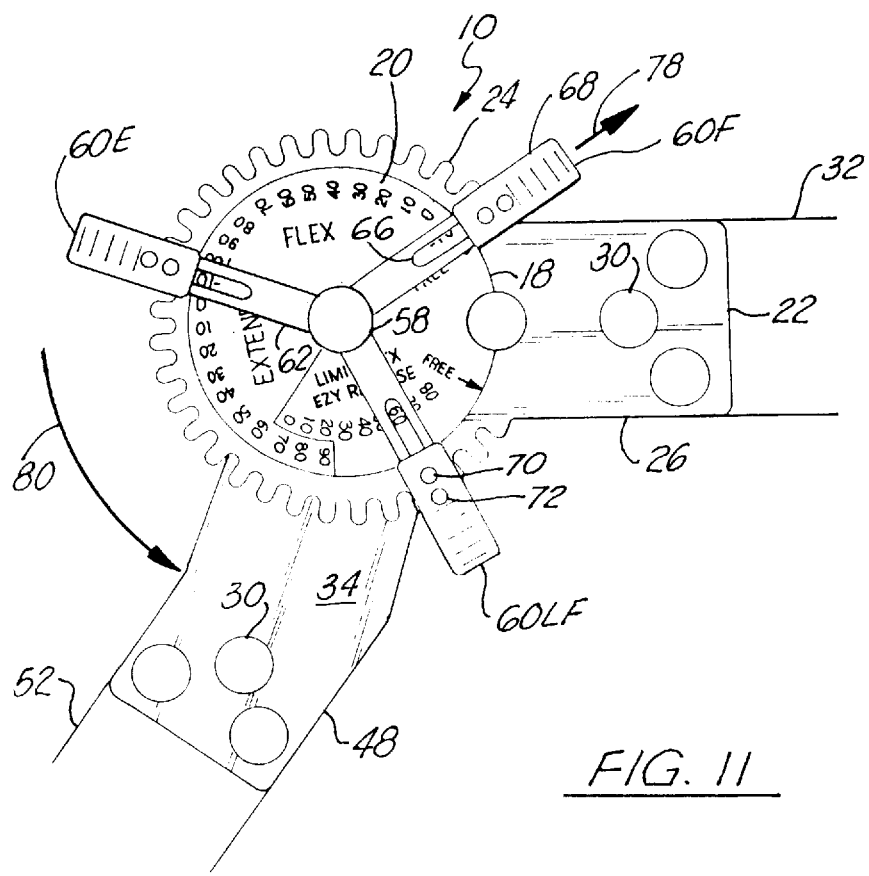
FIG. 11 is a front pictorial view of the invention illustrating how the locked position of the brace may be temporarily suspended.
Figure 12:
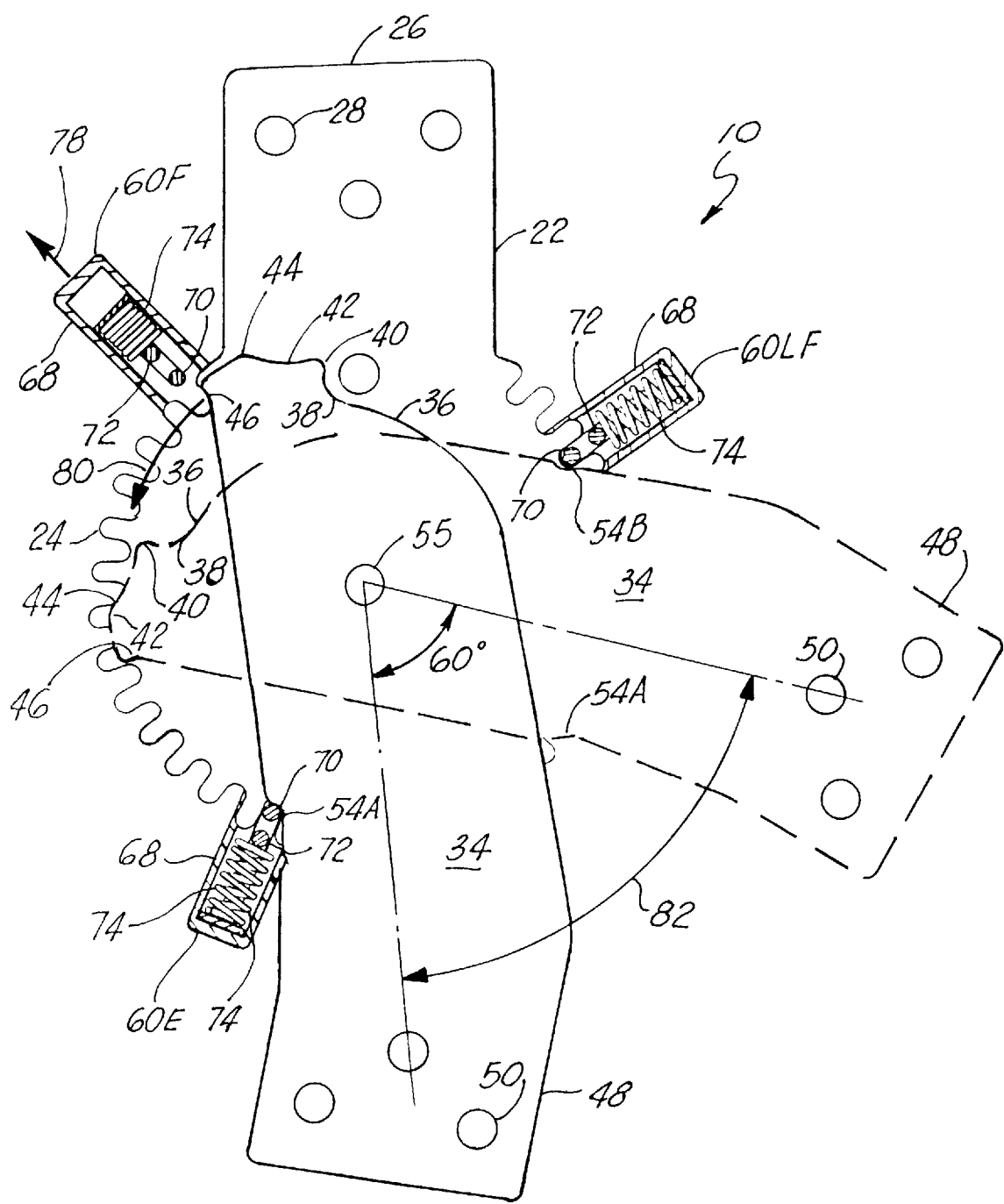
FIG. 12 is a pictorial view of the invention similar to that shown in FIG. 11, but with a portion of the invention cut away.

However, should a situation arise when it is imperative that knee 14 be temporarily released from this locked position, brace 10 can accommodate this need as well. As shown in FIGS. 11 and 12, such temporary release is achieved by simply grasping cap 68 of flex sliding latch 60F and pulling it outward in the direction of arrow 78. This action moves both inner and outer pins 70 and 72 outward thereby compressing spring 74 and lifting inner pin 70 from between teeth 24 as shown. When inner pin 70 of flex sliding latch 60F is thus moved, the counter-clockwise restraint on lower leg support 34 is effectively removed thereby permitting it to now pivot in the direction of arrow 80. Knee 14 will now be permitted to flex as desired.

For safety reasons, however, it is often desirable to place a limit on this permitted temporary flex or rotation of knee 14. Such limit is achieved as shown in FIGS. 11 and 12 by positioning limit flex sliding latch 60LF at the maximum angle permitted. In this embodiment, this maximum angle is set at 60 degrees as indicated by indica 20 visible through elongated slot 66 of limit flex sliding latch 60LF of FIG. 11. Thus, lower leg support 34 is permitted to flex along arc 82 about center rivet 58 until notch 54B engages inner pin 70 of limit flex sliding latch 60LF as shown in FIG. 12. This limit flex sliding latch 60LF thus effectively restricts any further counter-clockwise rotation of lower leg support 34. Knee 14 is now able to freely bend within the range between the selected positions of extension and limit flex sliding latches 60E and 60LF.

When the time comes to return brace 10, and hence knee 14, to its original fixed or braced position, the user simply pivots knee 14 back to this position. This oftentimes occurs by simply making knee 14 weight-bearing once again. The return of knee 14 to its original braced position causes brace 10 to automatically lock once again at the original settings thereby preventing any further rotation or flex of knee 14 unless such restraint is removed as discussed above.

Figure 14:
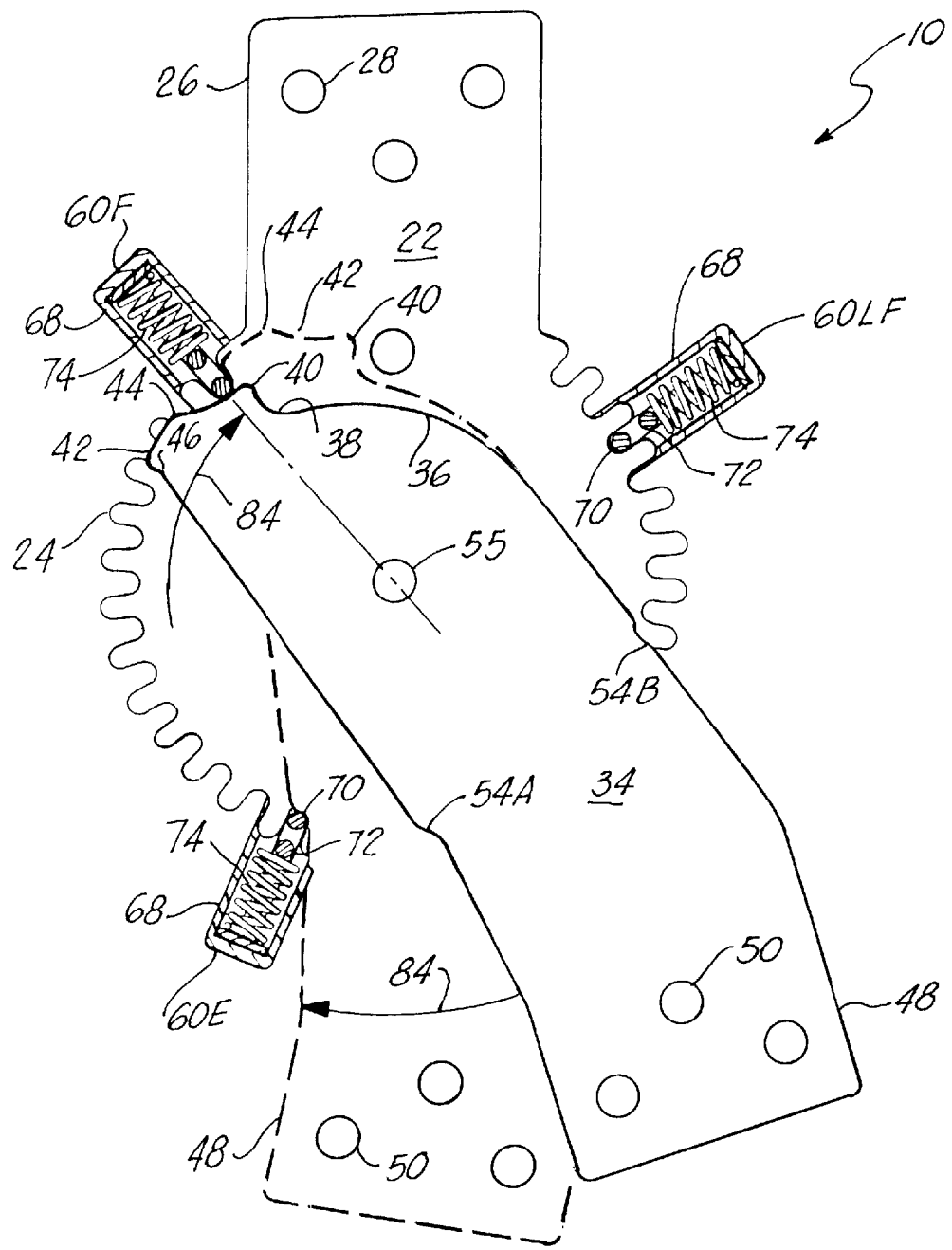

FIGS. 13 and 14 illustrate the step of automatically returning brace 10 to its original braced position. As shown, lower leg support 34 is rotated by the user in the direction of arrows 84. This results in tapered surface 42 engaging inner pin 70 of flex sliding latch 60F. Continued rotation of lower leg support 34 causes tapered surface 42 to lift or move pin 70 outward thereby allowing pin 70 to pass over bulge 44 and come to rest once again within recess 46. Likewise, the continued rotation of lower leg support 34 will cause notch 54A to again contact inner pin 70 of extension sliding latch 60E. Consequently, lower leg support 34 will be automatically returned to the locked position previously shown in FIGS. 9 and 10. Hence, knee 14 will once again be restrained in a locked or braced position. To release knee 14 from this locked position, the user need merely release the restraint imposed upon brace 10 via flex sliding latch 60F as previously described with respect to FIGS. 11 and 12.

As can be imagined, many different settings of sliding latches 60 can be implemented to achieve a great variety of support and/or restraint by brace 10. For example, both extension and flex sliding latches 60E and 60F can be set at 20 degrees while limit flex sliding latch 60LF is set at 30 degrees. Accordingly, knee 14 is retained at a 20 degree angle when brace 10 is in the locked position. However, when this restraint is removed as indicated in FIGS. 11 and 12, the maximum permitted bending of knee 14 will be 30 degrees. Thus, when released from such restraint, knee 14 will only be able to bend in an arc of between 20 and 30 degrees. Many other such settings are possible.

When restraining knee 14 at a fixed angle, it is important that both extension and flex sliding latches 60E and 60F be set the same (i.e. the same value of indica 20 should appear through their respective elongated slots 66). In the event extension and flex sliding latches 60E and 60F are not set the same, then knee 14 will be permitted to bend between the angles at which these sliding latches are set. For example, should extension sliding latch 60E be set at 0 degrees and flex sliding latch 60F set at 20 degrees, then knee 14 will be permitted to bend between 0 and 20 degrees without the necessity of releasing restraint as indicated in FIGS. 11 and 12. However, should such restraint be removed by disengaging flex sliding latch 60F, then knee 14 will be permitted to bend up to the limit set by limit flex sliding latch 60LF. This feature is useful when knee 14 need not be restrained at one single position but instead can be permitted to bend along a small arc but must still be prevented from bending too much. However, when it becomes imperative that even this range of permitted movement must be increased, the restraint imposed by flex sliding latch 60F can be released thereby increasing the range of movement of knee 14 up to the setting of limit flex sliding latch 60LF.

In the event there is no need to impose a maximum limit on the temporary bending of knee 14, such as the one imposed by limit flex sliding latch 60LF, then this latch 60LF can be re-positioned to the 'free' setting on decal 18. Such a positioning of limit flex sliding latch 60LF will mean that the user, when the restraint imposed by brace 10 is suspended, will be able to bend knee 14 to whatever angle is desired. Limit flex sliding latch 60LF will no longer impose or impart a restraint upon the bending of knee 14.

Likewise, should flex sliding latch 60F be repositioned to its respective 'free' position, then there would no longer be any restraint imposed upon knee 14 by this sliding latch and the only restraint available would be that provided by extension sliding latch 60E and limit flex sliding latch 60LF (assuming latch 60LF is not also at its 'free' position). For example, should extension sliding latch 60E be set at 20 degrees and should both flex sliding latch 60F and limit flex sliding latch 60LF each be at the 'free' position, then knee 14 will be able to bend freely but will not be permitted to straighten out or extend at an angle greater than 20 degrees. On the other hand, should extension sliding latch 60E be set at 20 degrees and should flex sliding latch 60F be set at 'free' and should limit flex sliding latch 60LF be set at 50 degrees, then leg 12 will only be able to extend to an angle of 20 degrees and will only be able to flex to an angle of 50 degrees.

The same result as imposed by this latter example can also be achieved by setting extension sliding latch 60E to 20 degrees and setting both latches 60F and 60LF to 50 degrees. Thus, leg 12 can extend only to 20 degrees and will only be able to flex to 50 degrees regardless of whether an attempt is made to release restraint or not by lifting flex sliding latch 60F. In this last example, when leg 12 is extended to 20 degrees the operation of brace 10 is as follows. Inner pin 70 of extension sliding latch 60E engages notch 54A of lower leg support 34 thereby preventing any further extension of support 34. On the other hand, when leg 12 is flexed to 50 degrees, two restraints are imposed. First, inner pin 70 of flex sliding latch 60F engages recess 46 of lower leg support 34 and inner pin 70 of limit flex sliding latch 60LF engages opposite notch 54B of lower leg support 34. Either or both such restraints stop or prevent any further rotation or flex of lower leg support 34 about center rivet 58.

As noticed in each of the above examples of typical set-ups of brace 10, extension sliding latch 60E is set at a degree value equal to or less than the setting of flex sliding latch 60F. Thus, when adjusting brace 10, it is important to first set extension sliding latch 60E before setting flex sliding latch 60F so that the lower degree setting is associated with extension sliding latch 60E.

Furthermore, as indicated in FIG. 8, brace 10 incorporates cushion pad 86 which also functions to space brace 10 from knee 14. This cushion pad 86 and the gap it creates between brace 10 and knee 14 enables gear members 22 and 56 to rotate with respect to lower leg support 34. Pad 86 is generally affixed to base 88 which is supported in a position slightly spaced from the inner surface of inner gear member 56 so that lockout straps 62 of each of sliding latches 60 can rotate without any interference. This base 88 is generally supported by center rivet 58 and may or may not be rotatable.

While the above description is presented with respect to the user's knee 14, this brace 10 is, as indicated earlier, also equally suitable for other joints of the user such as the elbow, wrist, hip, foot and the like. The only change that is needed for these other joints is in the size and configuration of brace 10 since its operation would be the same. Also, while the above embodiment is described with two separate gear members 22 and 56, in reality there may only be a need for one such member or there may be a need for more than two such members. Other configurational changes to sliding latches 60 and lower leg support 34 are also anticipated since despite the final shape thereof, the operation and interrelationship of these various components would still be the same.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. An adjustable joint brace comprising:
   (a) a first gear member having a plurality of gear teeth along at least a portion of its outer periphery;
   (b) sliding latch means rotatable with respect to said first gear member for engaging said gear teeth, said sliding latch means comprising locking means for locking said sliding latch means with respect to selected said gear teeth;
   (c) an elongated support pivotally secured to said first gear member and configured to engage said locking means of said sliding latch means, said locking means restricting the rotation of said elongated support with respect to said first gear member, said locking means of each said sliding latch means comprise at least one movable pin sized to fit intermediate adjacent said gear teeth, said elongated support also being configured to engage said pin, thereby restricting the further rotation of said elongated support, said movable pin of each said locking means being biased to engage said gear teeth, said bias being overcome when said movable pin is moved to engage other said gear teeth;
   (d) securing means for securing said first gear member and said elongated support adjacent a user's joint, said securing means comprising closure means secured adjacent the joint to be braced;
   (e) indicia means attached to said first gear member for indexing the positioning of said sliding latch means with respect to said first gear member;
   (f) a plurality of said sliding latch means rotatable with respect to said first gear member;
   (g) a second gear member pivotally supported on an opposite side of said elongated support from said first gear member, said second gear member also having a plurality of gear teeth along at least a portion of its outer periphery;
   (h) a center fastening means pivotally securing said first and second gear members, said sliding latch means, and said elongated support together, said elongated support comprising a recess therein on one side of said center fastening means and a notch on an opposite side of said center fastening means, said recess and said notch each being equally radially spaced from said center fastening means and each being sized to engage a said movable pin therein, whereby when both said recess and said notch engage their respective movable pin, said elongated support is no longer pivotable with respect to said gear members; and,
   (i) a cushion means secured to said brace intermediate the user's joint and said brace.

2. The apparatus as set forth in claim 1, wherein at least one said sliding latch means comprises a cap for grasping said sliding latch means and overcoming said spring bias to remove said movable pin from between said adjacent gear teeth, thereby permitting said elongated support to rotate with respect to said gear members.

3. The apparatus as set forth in claim 2, further comprising a limit flex sliding latch which, when locked with respect to selected said gear teeth, limits the rotation of said elongated support when said elongated support is no longer restrained by said sliding latch means.

4. The apparatus as set forth in claim 3, wherein said elongated support comprises a tapered surface adjacent said recess for engaging a said movable pin and lifting said movable pin from between said adjacent gear teeth, said tapered surface operating to return said elongated support back to the original settings or restraint imposed by said sliding latch means.

5. The apparatus as set forth in claim 4, wherein said sliding latch means comprise an extension sliding latch, a flex sliding latch and a limit flex sliding latch, said limit flex sliding latch being on a side of the brace opposite from said extension and said flex sliding latches.

6. The apparatus as set forth in claim 5, further comprising a free position for said flex sliding latch and a separate free position for said limit flex sliding latch wherein when said flex sliding latch or said limit flex sliding latch is positioned at its respective said free position, the respective movable pins do not engage said elongated support thereby imposing no restraint on the rotation of said elongated support.

7. An adjustable joint brace comprising:
   (a) first and second gear members having a plurality of gear teeth along a portion of their outer periphery, said first and second gear members being affixed to each other;
   (b) an elongated support pivotally sandwiched intermediate said first and second gear members, said elongated support being rotatable with respect to said first and second gear members via a center rivet;
   (c) an extension sliding latch, a flex sliding latch, and a limit flex sliding latch all pivotally secured around said first and second gear members and independently rotatable about said center rivet, said extension and said flex sliding latch being on a side of the brace opposite said limit flex sliding latch;
   (d) locking means secured to each said sliding latch for locking said sliding latch with respect to selected said gear teeth, each said locking means comprising a movable pin positioned intermediate adjacent said gear teeth for engaging said elongated support and restricting the rotation of said elongated support with respect to said gear members; and,
   (e) securing means for securing said first gear member and said elongated support adjacent a user's joint.

8. The apparatus as set forth in claim 7, further comprising indicia means attached to said first gear member for indexing the position of said sliding latches with respect to said first gear member.

9. The apparatus as set forth in claim 8, wherein each said movable pin is spring biased to engage said gear teeth, said spring bias being overcome when said movable pin is moved to engage other said gear teeth.

10. The apparatus as set forth in claim 9, wherein said securing means comprise hook and loop closure straps secured adjacent the joint to be braced.

11. The apparatus as set forth in claim 10, further comprising a cushion pad secured to the brace intermediate the user's joint and the brace.

12. The apparatus as set forth in claim 11, wherein said elongated support is configured with a recess therein on one side of said center rivet, a first notch on an opposite side of said center rivet, and a second notch on a side of said elongated support opposite said first notch, said recess and said first and second notches each being equally radially spaced from said center rivet and each being sized to engage a said movable pin therein to restrict the further rotation of said elongated support about said center rivet.

13. The apparatus as set forth in claim 12, wherein each said sliding latch comprises a cap for grasping said sliding latch and overcoming said spring bias to remove said movable pin from between said adjacent gear teeth thereby removing restrain on said elongated support.

14. The apparatus as set forth in claim 13, further comprising a free position for said flex sliding latch and a separate free position for said flex limit sliding latch wherein when said flex sliding latch or said limit flex sliding latch is positioned at its respective said free position, the respective movable pins do not engage said elongated support thereby imposing no restraint on the rotation of said elongated support.

* * * * *